United States Patent [19]
Martin et al.

[11] Patent Number: 5,117,146
[45] Date of Patent: May 26, 1992

[54] ACOUSTIC WAVE DEVICE USING PLATE MODES WITH SURFACE-PARALLEL DISPLACEMENT

[75] Inventors: Stephen J. Martin; Antonio J. Ricco, both of Albuquerque, N. Mex.

[73] Assignee: The United States of America as represented by the United States Department of Energy, Washington, D.C.

[21] Appl. No.: 719,654

[22] Filed: Jun. 21, 1991

Related U.S. Application Data

[63] Continuation of Ser. No. 187,776, Apr. 29, 1988, abandoned.

[51] Int. Cl.$^5$ ............................................. H01L 41/08
[52] U.S. Cl. ................................. 310/313 R; 310/312; 73/23.2; 73/24.01; 73/32 A; 73/597
[58] Field of Search ..................... 310/311, 312, 313; 333/150-155, 193-196; 73/596, 597, 599, 23.2, 23.28, 23.33, 23.36, 23.37, 23.4, 24.01, 24.04, 24.05, 24.06, 25.04, 25.05, 28.01, 30.01, 30.04, 53; 375/117, 119

[56] References Cited

U.S. PATENT DOCUMENTS

| | | | |
|---|---|---|---|
| 2,439,130 | 4/1948 | Firestone | 73/67 |
| 3,987,378 | 10/1976 | Onodera | 310/313 R X |
| 4,117,716 | 10/1978 | Simon | 73/32 A |
| 4,210,722 | 7/1980 | Silver | 310/311 X |
| 4,233,849 | 11/1980 | Defebvre et al. | 73/812 |
| 4,246,344 | 1/1981 | Silver, III | 310/311 X |
| 4,294,105 | 10/1981 | Kelly | 310/311 X |
| 4,312,228 | 1/1982 | Wohltjen | 310/313 R X |
| 4,325,255 | 4/1982 | Howard et al. | 73/589 |
| 4,361,026 | 11/1982 | Muller et al. | 73/23 |
| 4,372,163 | 2/1983 | Tittmann et al. | 73/602 |
| 4,378,168 | 3/1983 | Kuisma et al. | 374/28 |
| 4,454,440 | 6/1984 | Cullen | 310/313 R |
| 4,471,296 | 9/1984 | Dalgaard | 310/311 X |
| 4,504,758 | 3/1985 | Wisbey | 310/313 R |
| 4,539,846 | 9/1985 | Grossman | 73/579 |
| 4,598,224 | 7/1986 | Ballato | 310/313 R |
| 4,691,714 | 9/1987 | Wong et al. | 128/738 |
| 4,726,225 | 2/1988 | Brace et al. | 310/313 R X |
| 4,789,804 | 12/1988 | Karube et al. | 310/311 |
| 4,932,255 | 6/1990 | Brace et al. | 310/313 R X |

FOREIGN PATENT DOCUMENTS 0860283 8/1981 U.S.S.R. .............................. 333/151

OTHER PUBLICATIONS

"Surface Acoustic Wave Devices as Chemical Sensors in Liquids, Evidence Disputing the Importance of Rayleigh Wave Propagation", by G. Calabrese et al., *Analytical Chemistry*, vol. 59, No. 6, Mar. 15, 1987, pp. 833-837.

J. Roederer & G. Bastiaans, "Microgravimetric Immunoassay with Piezoelectric Crystals", *Analytical Chemistry*, vol. 55, No. 14, Dec. 1983, pp. 2333-2336.

K. Kanazawa & J. Gordon, II, "The Oscillation Frequency of a Quartz Resonator in Contact with a Liquid", *Analytica Chimica Acta*, vol. 175, 1985, pp. 99-105.

S. Martin et al., "Acoustic Wave Devices for Sensing in Liquids", *Transducers '87*, distributed Jun. 2, 1987.

A. Barendsz et al., "A SAW'-Chemosensor for NO2 Gas-Concentration Measurement", 85 *Ultrasonics Symposium*.

A. Bryant et al., "Gas Detection Using Surface Acoustic Wave Delay Lines", *Sensors and Actuators*, vol. 4, 1983, pp. 105-111.

K. Yen et al., "Recent Advances in Shallow Bulk Acoustic Wave Devices", 1979 *Ultrasonics Symposium*, pp. 776-785.

*Primary Examiner*—Mark O. Budd
*Attorney, Agent, or Firm*—Karla Ojanen; James H. Chafin; William R. Moser

[57] ABSTRACT

Solid-state acoustic sensors for monitoring conditions at a surface immersed in a liquid and for monitoring concentrations of species in a liquid and for monitoring electrical properties of a liquid are formed by placing interdigital input and output transducers on a piezoelectric substrate and propagating acoustic plate modes therebetween. The deposition or removal of material on or from, respectively, a thin film in contact with the surface, or changes in the mechanical properties of a thin film in contact with the surface, or changes in the electrical characteristics of the solution, create perturbations in the velocity and attenuation of the acoustic plate modes as a function of these properties or changes in them.

15 Claims, 3 Drawing Sheets

ACOUSTIC WAVE DEVICE USING PLATE MODES WITH SURFACE-PARALLEL DISPLACEMENT

FIELD OF THE INVENTION

This invention relates to acoustic sensor devices, and more particularly to acoustic sensor devices utilizing acoustic plate modes with components of displacement parallel to a crystal surface. The United States Government has rights in this invention pursuant to Contract No. DE-AC0476DP00789 between the Department of Energy and AT&T Technologies, Inc.

This is a continuation of application Ser. No. 187,776 filed Apr. 29, 1988 now abandoned.

BACKGROUND OF THE INVENTION

Acoustic waves (AW) in piezoelectric structure have been used to measure liquids in contact with the piezoelectric structure. For example, U.S. Pat. No. 4,378,168 of H. Kuisma. Mar. 29, 1983, discloses a piezoelectric device having spaced input and output electrodes on a surface for generating a surface acoustic wave (SAW) that detects the presence of humidity between the electrodes as a function of signal attenuation. However, this device does not provide an indication of any properties of condensed liquid.

The use of devices which use the Rayleigh wave, or SAW, to sense mass changes at solid/gas interfaces is known. However, the SAW is impractical for use in detection at solid/liquid interfaces because the Rayleigh wave they employ does not propagate efficiently at a solid-liquid interface. The Rayleigh wave has a surface-normal component of particle displacement which generates compressional waves in a liquid, leading to substantial attenuation of the wave.

U.S. Pat. No. 4,691,714 of J. Wong et al., Sep. 8 1987, discloses the use of a bulk acoustic wave within a piezoelectric structure to measure viscosity of a liquid in contact with the structure. The viscosity of the liquid is a function of the amplitude of the transmitted bulk acoustic signal, and the temperature of the liquid (actually, the temperature of the sensing transducer) is a function of the phase of the SAW that is also transmitted in this device.

SUMMARY OF THE INVENTION

It is an object of the present invention to provide an acoustic wave sensor for monitoring and quantifying the concentration of species in a solution by chemically modifying the sensor surface with a material or substance which selectively adsorbs or absorbs the solution species.

It is a further object of the present invention to provide an acoustic wave sensor for monitoring and quantifying the deposition and removal of material from a surface immersed in a liquid.

It is another object of the present invention to provide an acoustic sensor for monitoring and quantifying the variations in solution electrical characteristics, including ionic conductivity and dielectric coefficient.

Additional objects, advantages, and novel features of the invention will become apparent to those skilled in the art upon examination of the following description or may be learned by practice of the invention. The objects and advantages of the invention may be realized and attained by means of the instrumentalities and combinations particularly pointed out in the appended claims.

To achieve the foregoing and other objects, and in accordance with the purpose of the present invention, as embodied and broadly described herein, the present invention may comprise a piezoelectric substrate having a pair of opposed surfaces, with spaced input and output transducers affixed to the substrate for propagating acoustic plate modes through said substrate. Means are provided for maintaining a liquid in contact over a predetermined portion of a surface, or a film on a surface, of said substrate, the liquid creating perturbations in the velocity of the acoustic plate modes passing along the surface. An rf signal is applied to the input transducer and received at the output transducer. Means are also provided for determining the velocity perturbations from the rf signals, the perturbations being an indication of the conditions being monitored.

IN THE DRAWINGS

Figure 1:
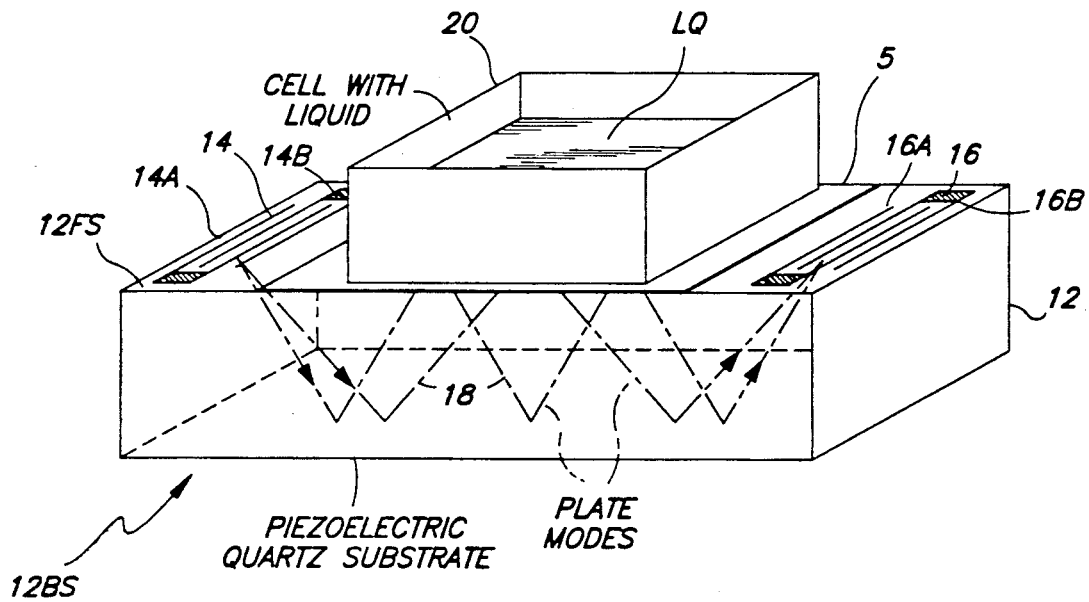
FIG. 1 is an enlarged schematic in perspective of an acoustic sensor of the present invention, showing the use of the front face of the crystal.
Figure 2:
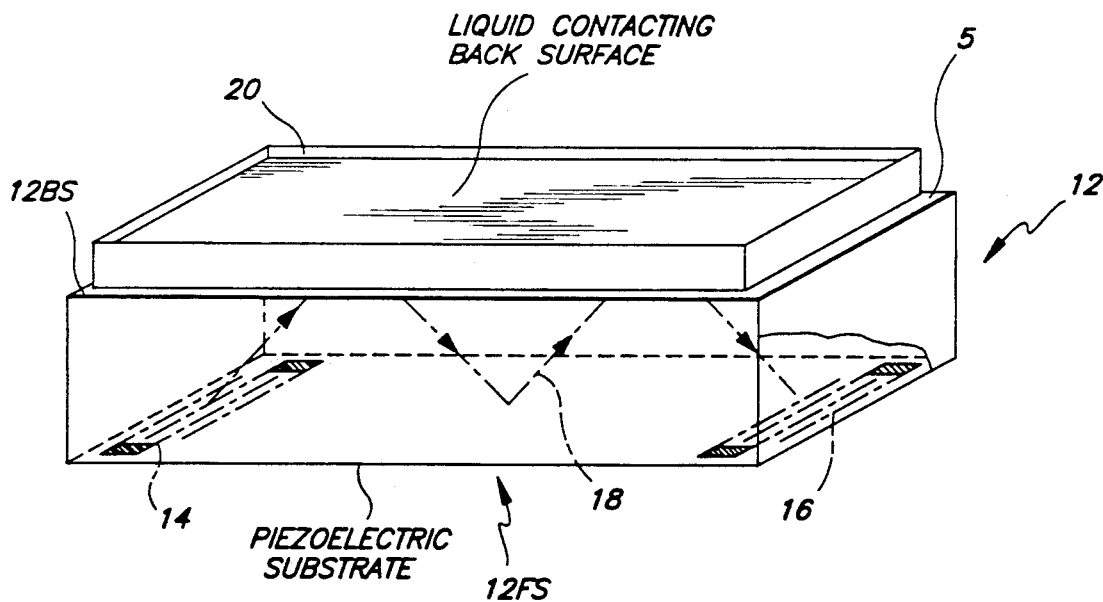
FIG. 2 is an enlarged schematic in perspective of an acoustic sensor of the present invention, showing the use of the back face of the crystal.
Figure 5:
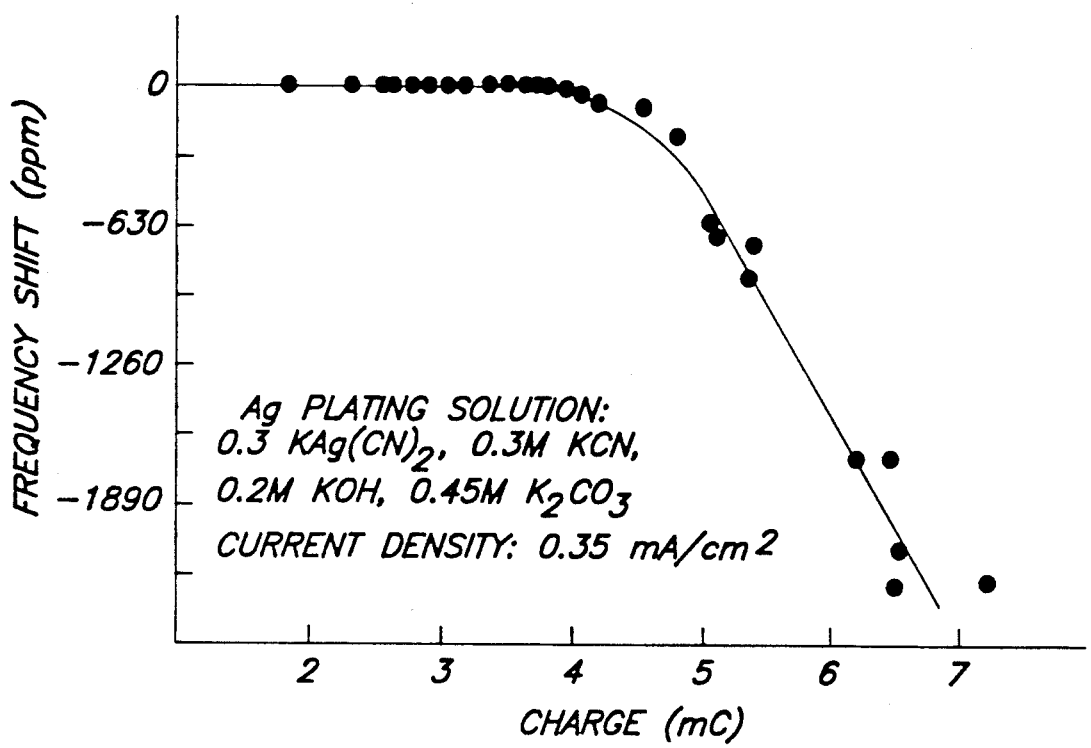
Figure 6:
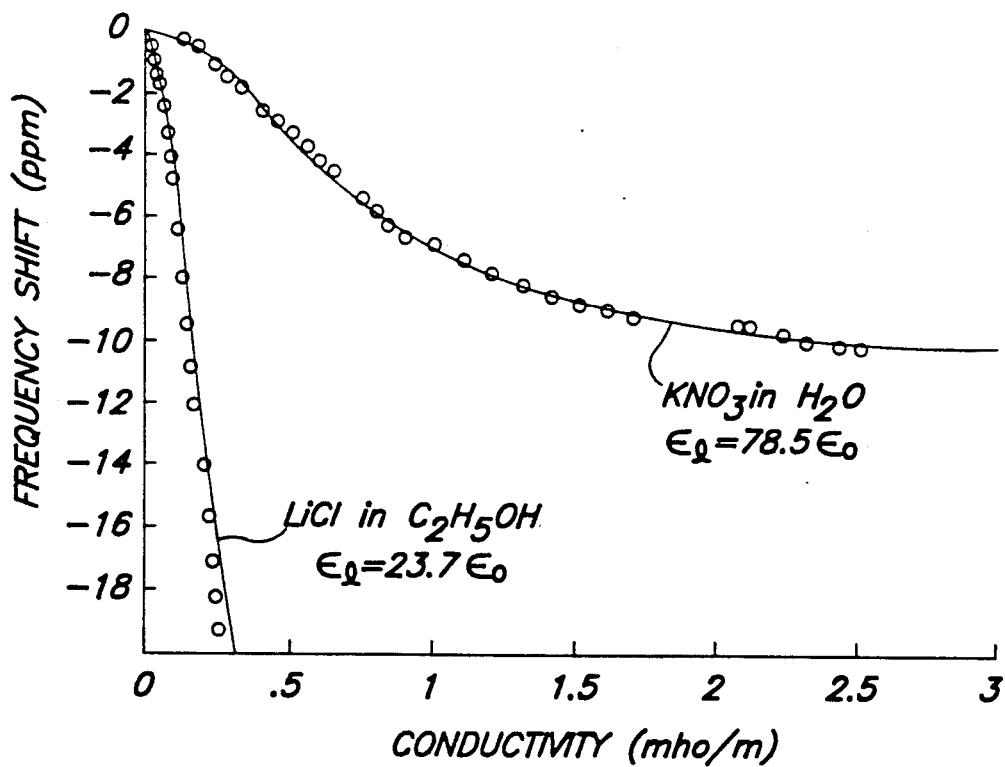

FIG. 5 is a graph illustrating that the velocity of propagation of the APM in FIGS. 1 and 2 is a function of the amount of material deposited by a given charge in the electrode position of Ag on a Pd electrode on the crystal surface; and FIG. 6 is a graph illustrating that the velocity of propagation of the APM in FIGS. 1 and 2 is a function of the ionic concentration and the dielectric coefficient of the solution.

DETAILED DESCRIPTION OF THE DRAWINGS

The purpose of this invention is to sense properties of solution species which may be dissolved in a liquid, deposited onto a surface immersed in a liquid, or removed from a solid surface immersed in a liquid. The invention is practiced by adsorbing, absorbing, or plating the solution species onto a acoustic wave device surface, or by desorbing, dissolving, or corroding a species from the device surface into solution, or by monitoring the extent and nature of acoustoelectric interactions between the AW and the solution and species in the solution.

The invention is fabricated on a piezoelectric single or polycrystalline substrate having a surface portion which may be coated with a material providing enhanced selectivity and/or sensitivity to a particular solution species. In the case of corrosion and electro deposition sensors, the immersed region is coated with a metal or other conductive electrode material to which electrical contact is made for the purpose of monitoring or applying a potential or current during the process of corrosion or electro deposition. Change in the amount of species on the device surface is detected through the perturbation of an acoustic plate mode propagating through the crystal and having in-plane displacements at the solid-liquid interface.

The capability and sensitivity of such detection and monitoring devices for sensing in liquids is dependent upon the use of the appropriate acoustic mode. The optimum mode in the present invention consists of one, or a superposition of more than one, acoustic plate modes (APMs). Plate modes are so-called because the acoustic wave reflects back and forth between the two faces of the crystalline plate while propagating along the length of the crystal.

On certain substrates, including particular cuts of quartz and lithium niobate, it is possible to excite acoustic plate modes by means of an interdigital transducer. In particular, APMs having displacement components at both crystal surfaces which lie only in the plane of these surfaces, and which therefore propagate efficiently at a solid-liquid interface, can be excited. The APMs propagate efficiently in the presence of liquids due to the absence of surface-normal components of particle displacement.

Addition of mass to either of the surfaces of the APM sensor slows the velocity of the acoustic wave to less than that of the unperturbed substrate. Conversely, if mass is initially added to either of the device surfaces, e.g., in the form of a thin film, the subsequent removal of a fraction or all of said mass causes the wave velocity to increase, the velocity reaching its unperturbed value when all the added mass has been removed. In addition, changes in the mechanical properties, including the stiffness, elasticity, and shear modulus, of a thin film in intimate contact with the APM sensor surface, result in perturbations of the acoustic wave velocity. Such changes in wave velocity resulting from change in surface mass and/or surface mechanical properties are analogous to those experienced by conventional SAW sensors operating in contact with the gas phase. The difference in the case of this invention is that these mass and mechanical changes can be readily measured while the device is in direct contact with a liquid, a measurement not readily made with a Rayleigh wave device.

Referring in detail to the drawings and with particular reference to FIGS. 1 and 2, the solid-state acoustic sensor is shown as including a generally rectangular piezoelectric substrate 12 with parallel front and back surfaces 12FS and 12BS on which are positioned an interdigital input transducer array 14 and an interdigital output transducer array 16. The arrows 18 within the substrate 12 indicate some, but not all, of the paths which may be taken by the APMs transmitted from the input transducer 14 to the output transducer 16 when an appropriate electrical signal is applied to input transducer array 14, as discussed hereinafter.

The front surface 12FS of the substrate 12 carries the input and output transducer arrays 14 and 16, which arrays are respectively positioned at opposite ends of the rectangular substrate 12. Each of the transducer arrays is formed of interdigitated elongated sets of fingers 14A-14B and 16A-16B arranged perpendicular to the plane containing the arrows 18 representative of the path of the wave; i.e., the transducers are normal to the direction of propagation of the APMs.

Either the front surface 12FS (FIG. 1) or the back surface 12BS (FIG. 2) is interfaced with a liquid LQ (shown by shading) confined in a cell structure 20 which comprises a liquid container for providing a liquid interface over a defined portion of one of the substrate surfaces 12FS or 12BS. When the liquid is interfaced with the front surface 12FS, the cell containing said liquid is located intermediate the input and output transducer arrays 14 and 16. No such restriction is placed on the location of the cell when the liquid is interfaced with the back surface 12BS of the substrate, the only requirement being that the liquid LQ contact some portion of the propagation path of the APMs.

A thin film 5, illustrated in each of FIGS. 1 and 2, may be placed between liquid LQ and substrate 12 as discussed hereinafter.

For either embodiment, cell 20 may either be a relatively low-walled structure, as shown, into which a sample of liquid LQ may be placed. Alternatively, cell 20 may represent one end of a tubular structure (not shown), the other end of which structure being connected to a container of the liquid LQ under test.

The input and output transducer pair 14, 16 defines an acoustic delay line. While only one such delay line is illustrated on the substrate 12, two such transducer pairs may be provided with one pair being a reference standard compensating for changes in ambient parameters such as temperature, pressure, density and the like, and the other pair, as illustrated, being for sensing the characteristics being monitored.

While the APM sensor is in contact with a liquid, a fractional change in the velocity of the APMs will result from changes in sensor surface conditions including, but not limited to, changes in the characteristics of the sensor surface or a thin film of material upon said sensor surface due to adsorption, absorption, deposition, removal, or desorption of matter; or changes in the mechanical properties of a thin film or of the sensor surface itself.

Figure 3:
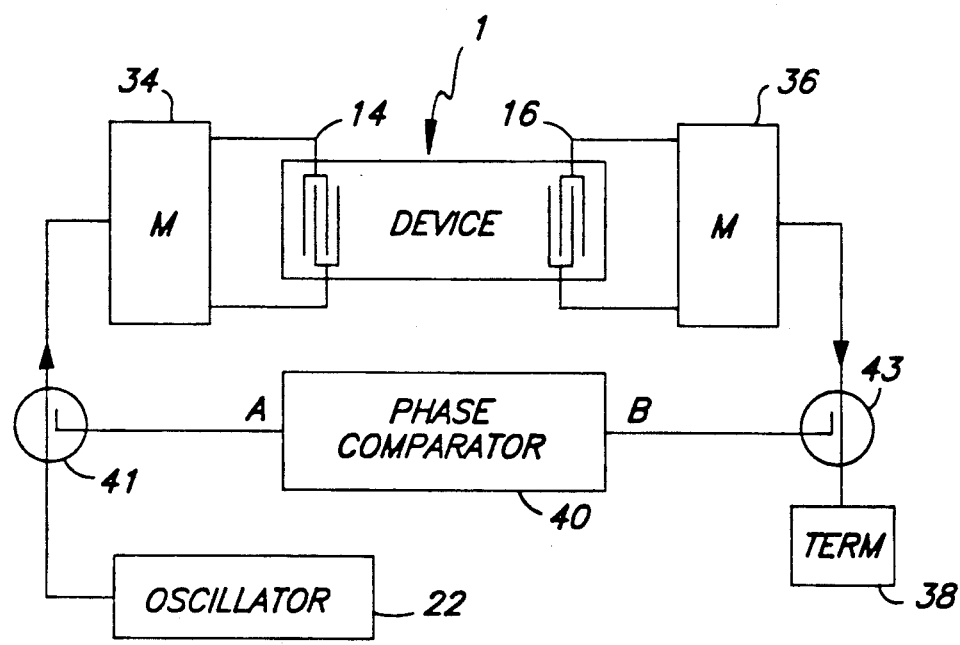
FIG. 3 is a schematic in plan view of one embodiment of an acoustic sensor of the present invention.

FIG. 3 illustrates one technique for measuring these fractional velocity changes. A radio frequency signal source 22 drives the fingers 14A, B of the input transducer 14 through an impedance matching transformer 34 to propagate the APMs from the input transducer 14 to the output transducer 16. The output transducer is terminated through another matching transformer 36 by a 50 ohm load 38. A vector voltmeter or phase-sensitive meter 40 equipped with two probes A, B monitors the phase difference between the acoustic wave incident upon the input transducer 14 and that received by the output transducer 16, providing a measure of the perturbations in wave velocity. Probes A, B are coupled to their respective signals through directional couplers 41, 43, respectively.

Figure 4:
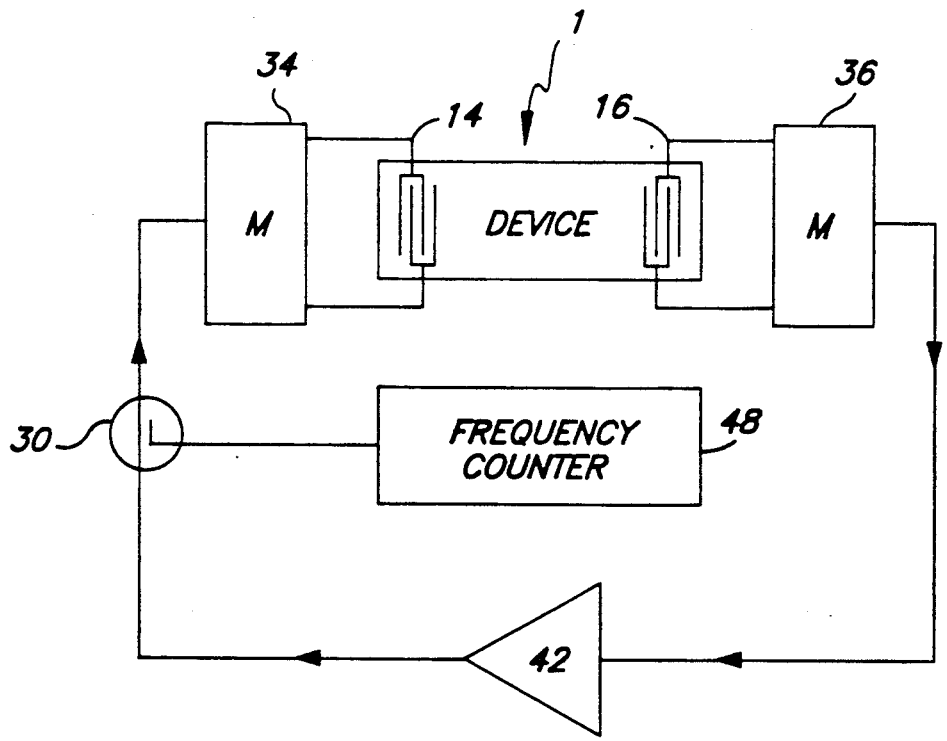
FIG. 4 is a schematic in plan view of a second embodiment of an acoustic sensor of the present invention.

Another measurement technique is shown in FIG. 4, where output transducer 16 is connected to input transducer 14 through an amplifier 42 suitable for operation at radio frequencies. A directional coupler 30 directs a fraction of the power incident on the input transducer 14 to a frequency counter 48 which provides a measure of the perturbations in wave velocity.

A specific example of the preferred embodiment of FIGS. 1 and 2 has been constructed. Substrate 12 was a polished single crystal of ST-cut quartz 0.5 mm (0.020) inches thick having a rectangular configuration 7.6 mm wide by 11.4 mm long (0.3×0.45 inches). The interdigital transducers 14A, B and 16A, B each had fifty (50) finger pairs wherein the fingers are 8 um wide and 1.675 mm long gold-upon-chromium lines, approximately 200 nm thick, separated by 8 um spaces and fabricated on the front surface 12FS of the substrate 12 by standard lithographic techniques.

The acoustic synchronous frequency (158 MHz) of the transducers 14, 16 is a function of the periodicity, d (32 um), of the interdigital patterns thereof, and the substrate material and thickness. This frequency is determined experimentally from the constructed device. Spacing between the input and output transducers 14 and 16 of each delay line on the substrate 12 is 6.4 mm (200 wavelengths).

The resulting sensor device was mounted in an 12 mm×25 mm (0.5×1.0) inch flatpack. Electrical connections to the device were made with gold wires bonded between the flatpack leads and bonding pads on the transducers 14, 16. The cell 20 for receiving the liquid LQ was made of polytetrafluoroethylene (Teflon) held to the surface 12FS using pressure from a metal fitting.

The input transducer 14, with periodicity d on substrate 12 of thickness b, excites efficiently a family of acoustic shear plate modes whose frequency spectrum is approximated by:

$$f_n = (v_o/2\pi)[(2\pi/d)^2 - (n\pi/b)^2]^{\frac{1}{2}} \quad (1)$$

in which $v_o$ is the velocity of the acoustic wave in a solid in the absence of bounding surfaces (5100 m/s for ST-quartz) and n is an integer (1, 2, 3, ... ). When the number of finger pairs N comprising the transducers 14, 16 is chosen such that $N > 4(b/d)^2$, the bandwidth of the transducers will be sufficiently narrow that each acoustic plate mode can be excited and detected individually; otherwise, a superposition of more than one plate mode is excited and detected.

The APMs can be used to measure the mass and mechanical properties of material present upon the sensor surface, or deposited from (or removed into) a liquid in direct contact with either sensor surface. The perturbation in APM wave velocity depends both on changes in surface mass and stiffness properties, with the fractional velocity perturbation given by:

$$\Delta v/v_o = -c_m \delta_m + F(\beta, u) \quad (2)$$

in which $c_m$, the mass sensitivity factor of the device, is given approximately by $v_o^2/(c_{44}b)$, where $v_o$ is the unperturbed operating velocity and $c_{44}$ is a stiffness parameter for the plate material; $\delta_m$ is the accumulated mass per unit area; and F is a function of the bulk modulus $\beta$ and shear modulus u of material on the surface.

When the wave velocity in any layer accumulating on or present on the sensor surface is much less than the wave velocity in the sensor substrate 12, this layer and any changes in it will have a negligible effect on the acoustic wave velocity via mechanical properties. Equation 2 then reduces to a simpler form:

$$\Delta v/v_o = -c_m \delta_m \quad (3)$$

In this case, the fractional change in velocity, and thus oscillation frequency, is linearly proportional to changes in surface mass. A convenient and precise way to monitor wave velocity is to incorporate the APM device as the feedback element in an oscillator loop as shown in detail in FIG. 4. The oscillation frequency of such a loop tracks and is linearly proportional to the acoustic wave velocity, so that fractional changes in the latter can be measured with parts per billion accuracy. The fractional change in frequency is equal to the fractional change in velocity given in Equations 2 and 3, above, times the fraction of the APM propagation path which experiences a change in mass and/or mechanical properties.

The signal represented by Equations 2 and 3 adds to the (constant) shift arising from the entrainment of liquid through viscous coupling. The APM sensitivity is greatest when b, the plate thickness, is minimized.

Referring now to FIGS. 1 and 2, the sensor 10 of the present invention is shown as it is adapted for sensing electrode reactions such as plating, corrosion, and the like, wherein the fluid LQ in the cell 20 is an electrolyte and the surface 12FS, BS of the portion of substrate 12 subtended by cell 20 is covered with a thin film 5 constituting an electrode or reacting surface. In a similar manner, monitoring of so-called electroless plating, in which a chemical reaction within the electrolyte solution results in the deposition of metal on a surface contacting the solution, may be accomplished without the need for a metal thin film on the sensor surface 12FS, BS provided the sensor surface is first sensitized with the chemicals commonly used to sensitize glass or plastic surfaces for such electroless metal deposition.

The thickness of any material(s), i.e., the thin film 5, deposited on the substrate should be no more than a few percent of the 32 um acoustic wavelength, thereby insuring that changes in wave velocity are linearly related to mass changes. Thus, the thickness of the electrode, together with any electro deposited materials, may range from less than one Angstrom to approximately 1 um. Pd, Au, Al, and Cu have thus far been used as electrode materials.

To demonstrate the measurement of mass accumulated from solution, silver was electro deposited onto a palladium electrode (vacuum evaporated onto the quartz substrate). Since the deposition rate is controlled by the electrode current (galvanostatic control), direct calibration of the APM mass sensitivity was obtained by comparing the frequency shift with the charge passed for a plating process of known current efficiency. For the silver plating experiment, which has current efficiency near unity, electrolyte containing 0.3M $[Ag(CN)_2]^-$ and 0.3M free $CN^-$ in a basic solution was added to the electrochemical cell 20; a Ag wire served as counter electrode. Current density was $-0.3$ mA/cm$^2$.

FIG. 5 shows the fractional frequency change as a function of the charge passed for this embodiment. The APM monitor reveals an induction period during which no significant change in surface mass occurs. This period may be due to reductive dissolution of surface impurities and/or Pd hydride formation. After the induction period, the frequency changes at a rate of 1.0 ppm/uC.

To demonstrate the monitoring of an etching process, the dissolution of a 4200 Angstrom thick aluminum film in a 0.3% NaOH solution was followed as a function of time. A total frequency shift of 1280 ppm occurred over a period of approximately 4 min. With the exception of a few seconds at the beginning of the dissolution process, the etch rate was constant at 17 Angstroms/s until the Al had been completely removed.

Referring again to FIGS. 1 and 2, the sensor element 10 of the present invention may also be used to sense dissolved solution species by chemically derivatizing the quartz surface. For example, if the liquid is a solution containing dissolved species such as $Cu^{2+}$ and the thin film is a surface-immobilized reagent such as N-2-aminoethyl-3-aminopropyltrimethoxysilane, suitable to ligate said solution species, the perturbation in velocity of the acoustic plate modes will be a function of variations in concentration and identity of the solution species, the variations being reflected in the mass bound by the thin film on the device surface.

When a plate mode propagates in the piezoelectric quartz waveguide, the resulting mechanical deformation leads to the generation of evanescent rf electric fields which extend into the adjacent liquid environment. In a non-conductive liquid, the electric field decays exponentially with distance into the liquid, with a decay length of $\lambda/2\pi$ ($\lambda$ is the acoustic wavelength, 32 um). The mode velocity and attenuation are influenced by the interaction of this evanescent electric field with ions and dipoles in solution.

The velocity changes and attenuation $\alpha$ (per wavenumber k) arising from the interaction of the evanescent electric field with ions in solution are:

$$\frac{\Delta v}{v_0} = -\frac{K^2}{2}\left[\frac{\epsilon_s - \epsilon_0}{\epsilon_s - \epsilon_1}\right]\frac{\sigma^2}{\sigma^2 + \omega^2(\epsilon_s + \epsilon_1)^2} \quad (4a)$$

and $$\frac{\alpha}{k} = \frac{K^2}{2}\left[\frac{\epsilon_s - \epsilon_0}{\epsilon_s + \epsilon_1}\right]\frac{\sigma(\epsilon_s - \epsilon_1)}{\sigma^2 - \omega^2(\epsilon_s + \epsilon_1)^2} \quad (4b)$$

in which $K^2$ is the electromechanical coupling factor, a measure of the piezoelectric strength of the substrate; $\epsilon$ is the dielectric coefficient of the substrate s, liquid l, and free space o; $\omega$ is the angular frequency of oscillation, and $\sigma$ is the ionic conductivity of the solution.

Data have been obtained on the acoustoelectric interaction between plate modes and ions in solution. Velocity and attenuation were monitored while varying the ionic strength of a solution in contact with the device surface. While the attenuation change was too small to measure accurately, velocity decreased with increasing ionic strength, with the effect eventually saturating. Data are shown in FIG. 6 along with the result predicted by Equation 4a. The range of conductivities over which this effect is measurable, 0.01 to 0.3-$\Omega$-cm, should prove useful for monitoring ionic strength. It is apparent from FIG. 6 that the dielectric properties of the liquid will also influence the propagation velocity of the plate mode.

As can be seen from the foregoing specification and drawings, the present invention provides a new and novel solid-state acoustic sensor device for monitoring a variety of conditions at a liquid/surface interface. It should be noted that the cell 20 and reactive thin film 5 can be placed on either side of the sensor substrate 12, and that utilization of the back surface of the sensor 12BS allows protection of the transducer arrays 14 and 16 from corrosive environments, if desired. Thus, the versatility of the sensor devices is further enhanced.

The present invention having been thus described, it should be apparent that modifications could be made to the various components of the system, as would occur to one of ordinary skill in the art without departing from the spirit and scope of the present invention.

We claim:

1. A solid-state acoustic plate mode sensor comprising:
   (a) a piezoelectric substrate having a pair of opposed surfaces;
   (b) input transducer means affixed to said substrate for propagating acoustic plate modes through said substrate;
   (c) output transducer means affixed to said substrate for receiving acoustic plate modes propagated through said substrate from said input transducer means;
   (d) means for maintaining a liquid in contact over a predetermined portion of either or both surfaces of said substrate, said liquid creating perturbations in the velocity of said acoustic plate modes reflecting internally from said predetermined portion of said surface;
   (e) means for applying a rf signal to said input transducer;
   (f) means for receiving an rf signal from said output transducer; and
   (g) means for determining said velocity perturbations from said rf signals; and
   (h) means for monitoring and quantifying the concentration of a chemical species in said liquid resulting from sorption of said species onto or desorption from said surface.

2. The solid-state acoustic plate mode sensor of claim 1, wherein said input and output transducer means each comprise a pair of interdigital combs coplanar with one surface of said substrate.

3. The solid-state acoustic plate mode sensor of claim 1, wherein said means for maintaining a liquid comprises a liquid receiving cell having a liquid containing wall extending from a substrate surface.

4. The solid-state acoustic plate mode sensor of claim 1, wherein said predetermined portion of said surface is in intimate contact and covered by a thin film in contact with said liquid, said liquid causing changes on the surface of said film, said changes causing in-plane displacements at the film-liquid interface and perturbations in said acoustic plate modes in said substrate.

5. The solid-state acoustic plate mode sensor of claim 4, wherein said liquid is an electrolyte and said thin film is an electrode receiving material by electrodeposition; said perturbation in velocity of said acoustic plate modes being a function of variations in mass and mechanical properties of the material received by said electrode.

6. The solid-state acoustic plate mode sensor of claim 4, wherein said liquid is an electrolyte and said thin film is an electrode surrendering material by electrodissolution; said perturbation in velocity of said acoustic plate modes being a function of variations in mass and mechanical properties of the material surrendered by said electrode.

7. The solid-state acoustic plate mode sensor of claim 4, wherein said liquid is an electrolyte and said thin film is a metal film changing material by corrosion; said perturbation in velocity of said acoustic plate modes being a function of variations in mass and mechanical properties of the change in amount of material on said thin film.

8. The solid-state acoustic plate mode sensor of claim 4, wherein said liquid is a solution containing dissolved species and said thin film is a surface-immobilized reagent designed to ligate said solution species; said perturbation in velocity of said acoustic plate modes being a function of variations in concentration and identity of the solution species, such variations being reflected in the mass bound by said thin film on the device surface.

9. A solid state acoustic plate mode sensor comprising:
   (a) a piezoelectric substrate of thickness b having opposed parallel surfaces;
   (b) input interdigital transducer means having two combs, each of said comb having N fingers and a periodicity d, said transducer means affixed to and coplanar with one surface of said substrate, for propagating acoustic plate modes whose frequency spectrum can be approximated by:

$$f_n = (v_o/2\pi)[(2\pi/d)^2 + (n\pi/b)^2]^{\frac{1}{2}}$$

where $v_o$ is the velocity of said acoustic plate mode in an unbounded piezoelectric solid, n is an integer, and where $N > 4(b/d)^2$, said acoustic plate modes propagated through the thickness of said substrate and reflected from each of said parallel surfaces;

(c) output interdigital transducer means having two combs, each of said comb having N fingers and a periodicity d, said transducer means affixed to and coplanar with one surface of said substrate, for receiving said acoustic plate modes propagated through the thickness of said substrate;

(d) means for maintaining a liquid in contact over a predetermined portion of either or both surfaces of said substrate, said liquid creating perturbations in the velocity of said acoustic plate modes internally reflecting from said predetermined portion of said surface; and (e) means for applying a rf signal to said input transducer;

(f) means for receiving an rf signal from said output transducer; and (g) means for determining said velocity perturbations of said acoustic plate modes from said rf signals; and (h) means for monitoring and quantifying the concentration of a chemical species in said liquid resulting from sorption or desorption of said species onto or from said surface.

10. The solid-state acoustic plate mode sensor of claim 9, wherein said means for maintaining a liquid comprises a liquid receiving cell having a liquid containing wall extending from a substrate surface.

11. The solid-state acoustic plate mode sensor of claim 9, wherein said predetermined portion of said surface is covered by a thin film in contact with said liquid, said liquid causing changes on the surface of said film, said changes causing the perturbations in said acoustic plate modes in said substrate.

12. The solid-state acoustic plate mode sensor of claim 9, wherein said liquid is an electrolyte and said thin film is an electrode receiving material by electrodeposition; said perturbation in velocity of said acoustic plate modes being a function of variations in mass and mechanical properties of the material received by said electrode.

13. The solid-state acoustic plate mode sensor of claim 11, wherein said liquid is an electrolyte and said thin film is an electrode surrendering material by electrodissolution, said perturbation in velocity of said acoustic plate modes being a function of variations in mass and mechanical properties of the material surrendered by said electrode.

14. The solid-state acoustic plate mode sensor of claim 11, wherein said liquid is an electrolyte and said thin film is a metal film changing material by corrosion, said perturbation in velocity of said acoustic plate modes being a function of variations in mass and mechanical properties of the change in amount of material on said thin film.

15. The solid-state acoustic plate mode sensor of claim 11, wherein said liquid is a solution containing dissolved species and said thin film is a surface-immobilized reagent designed to ligate said solution species, said perturbation in velocity of said acoustic plate modes being a function of variations in concentration and identity of the solution species, such variations being reflected in the mass bound by said thin film on the device surface.

* * * * *